United States Patent [19]
Some et al.

[11] Patent Number: 5,841,148
[45] Date of Patent: Nov. 24, 1998

[54] IMAGE PROCESSING APPARATUS

[75] Inventors: Masato Some; Hiromi Shibata, both of Kanagawa-ken; Kunihiro Takahashi, Akita, all of Japan

[73] Assignee: Fuji Photo Film Co., Ltd., Kanagawa, Japan

[21] Appl. No.: 792,191

[22] Filed: Jan. 30, 1997

[30] Foreign Application Priority Data

Feb. 2, 1996 [JP] Japan .................................... 8-040643
Feb. 2, 1996 [JP] Japan .................................... 8-040644

[51] Int. Cl.$^6$ ............................................. G01N 23/04
[52] U.S. Cl. ........................ 250/584; 378/62; 378/98.12; 382/132
[58] Field of Search ........................... 382/132, 130; 378/62, 70, 78, 98.11, 98.12; 250/584

[56] References Cited

U.S. PATENT DOCUMENTS

| | | | |
|---|---|---|---|
| 4,870,692 | 9/1989 | Zuiderveld et al. | 382/6 |
| 5,048,103 | 9/1991 | Leclerc et al. | 382/44 |
| 5,647,360 | 7/1997 | Bani-Hashemi et al. | 128/653.1 |

Primary Examiner—David P. Porta
Assistant Examiner—David Vernon Bruce
Attorney, Agent, or Firm—Sughrue, Mion, Zinn, Macpeak & Seas, PLLC

[57] ABSTRACT

An image processing apparatus includes a temporary memory for two-dimensionally mapping and temporarily storing image data containing image data regions corresponding to at least two image regions having similar shape and stored in an image data storing section, a CRT for reproducing an image based on the image data stored in the temporary memory, a pixel specifying section for specifying pixels corresponding to at least two equivalent points in at least two image regions having similar shape in the image displayed on the CRT, a data correcting section for effecting, between micro region image data corresponding to micro regions including coordinates of the at least two pixels specified by the pixel specifying section as center coordinates, rotation and movement correction and enlargement/reduction magnification correction on the micro region image data in the image data corresponding to one image region so that a rotation angle and an enlargement/reduction magnification of the one image region coincide with those of a reference image region which is one of the at least two image regions, a template matching section for effecting template matching on the micro region image data corrected by the data correcting section and the micro region image data in the image data corresponding to the reference image region, and an affine converting section for effecting affine conversion on the image data stored in the temporary memory based on the result of the template matching effected by the template matching section. According to the thus constituted image processing apparatus, it is possible to accurately effect template matching within a short time period.

18 Claims, 9 Drawing Sheets

IMAGE PROCESSING APPARATUS

BACKGROUND OF THE INVENTION

The present invention relates to an image processing apparatus and, particularly, to such an apparatus which can effectively and accurately effect template matching on a plurality of images for superimposing a plurality of images produced based on image data and effecting inter-image calculation.

DESCRIPTION OF THE PRIOR ART

A radiographic diagnosis system using as a detecting material for detecting radiation a stimulable phosphor which can absorb, store and record the energy of radiation when it is irradiated with radiation and when it is then stimulated by an electromagnetic wave having a specified wavelength, can release stimulated emission whose light amount corresponds to the amount of radiation with which it was irradiated is known, which comprises the steps of storing and recording the energy of radiation transmitted through an object in a stimulable phosphor, scanning a stimulable phosphor layer with an electromagnetic wave to stimulate the stimulable phosphor, photoelectrically detecting the stimulated emission released from the stimulable phosphor to produce digital image signals, effecting image processing on the digital image signals and reproducing a radiation image on a display means such as a CRT or a recording material such as a photographic film (For example, Japanese patent Application Laid Open Nos. 55-12429, 55-116340, 55-163472, 56-11395, 56-104645 and the like).

Further, an autoradiographic image detecting system using the same stimulable phosphor as a detecting material for detecting radiation is known, which comprises the steps of introducing a radioactively labeled substance into an organism, using the organism or a part of the tissue of the organism as a specimen, placing the specimen and a radiographic film such as a high sensitivity type X-ray film together in layers for a certain period of time to expose the radiographic film thereto and obtaining locational information on the radioactively labeled substance in the specimen from the resolved pattern of the radiographic film (For example, Japanese Patent Publication No. 1-60784, Japanese Patent Publication No. 1-60782, Japanese Patent Publication No. 4-3952 and the like).

Furthermore, a chemiluminescent detecting system using as a detecting material for detecting light a stimulable phosphor which can absorb, store and record the light energy when it is irradiated with light and when it is then stimulated by an electromagnetic wave having a specified wavelength, can release stimulated emission whose light amount corresponds to the amount of light radiation with which it was irradiated is known, which comprises the steps of selectively labeling a fixed high molecular substance such as a protein or a nucleic acid sequence with a labeling substance which generates chemiluminescent emission when it contacts a chemiluminescent substance, contacting the high molecular substance selectively labeled with the labeling substance and the chemiluminescent substance, detecting the chemiluminescent emission in the wavelength of visible light generated by the contact of the chemiluminescent substance and the labeling substance and obtaining information relating to the high molecular substance such as genetic information (For Example, U.S. Pat. No. 5,028,793, British Patent Publication GB No. 2,246,197A and the like).

Moreover, an electron microscope detecting system using as a detecting material for an electron beam or radiation a stimulable phosphor which can absorb, store and record the energy of an electron beam or radiation when it is irradiated with the electron beam or radiation and when it is then stimulated by an electromagnetic wave having a specified wavelength, can release stimulated emission whose light amount corresponds to the amount of the electron beam or radiation with which it was irradiated is known, which comprises the steps of irradiating a metal or nonmetal specimen with an electron beam, detecting a diffraction image, transmission image or the like and effecting elemental analysis, composition analysis or structural analysis of the specimen, or irradiating the tissue of an organism with an electron beam and detecting an image of the tissue of the organism, and a radiographic diffraction image detecting process comprising the steps of irradiating a specimen with radiation, detecting a radiographic diffraction image and effecting structural analysis of the specimen (For example, Japanese Patent Application Laid open No. 61-51738, Japanese Patent Application Laid open No. 61-93538, Japanese Patent Application Laid open No. 59-15843 and the like).

As compared with conventional systems using photographic films, these systems are advantageous in that no chemical processing is necessary, that an image can be reproduced in a desired manner by effecting image processing on the obtained image data and that quantitative analysis can be done using a computer.

These systems using a stimulable phosphor sheet are sometimes required to produce a plurality of images from the same object, superimpose the thus produced images of a specified part of the object, effect superimpose processing and reduce noise or effect subtraction processing for producing an image in which only a specified portion is emphasized.

Such superimpose processing is effected not only between a plurality of images of the same object but between a plurality of images containing image regions of similar shape and it is further required for superimposing symmetrical image regions in an image containing symmetrical image regions such as an image of an encephalon slice. In all cases, the following problem similarly occurs.

In all cases, it is necessary to superimpose specified image regions in a plurality of images for effecting the above processing. However, in the systems using a stimulable phosphor sheet, an image is stored and recorded in a stimulable phosphor layer of the stimulable phosphor sheet and cannot be directly viewed. A method for superimposing specified image regions in a plurality of images has therefore been proposed, which comprises the steps of recording a marker for alignment located in a constant position with respect to each image together with the image in the stimulable phosphor sheet for accurately superimposing the specified image regions in the plurality of images and rotating and/or moving one of the images as the digital data based on the markers so as to superimpose it on other images (For example, Japanese Patent Application Laid Open No. 58-163338 and the like).

However, in this method, when an image is stored and recorded in the stimulable phosphor sheet, the marker for alignment has to be simultaneously is stored and recorded in the stimulable phosphor sheet. This is troublesome and the portion of the stimulable phosphor sheet in which the marker for alignment is stored and recorded cannot be utilized for producing image data.

Japanese Patent Application Laid open No. 6-165036 therefore proposes a method for superimposing a plurality of images comprising the steps of defining at least two regions of interest substantially common to the plurality of images on the plurality of images to be aligned, determining the region of interest of a reference image as a reference region and other region of interest as a template region, defining a rectangular coordinate system in each image, effecting template matching for matching the template region with the reference region, determining at least two corresponding points in the plurality of images, determining a coefficient of affine conversion for converting the coordinate value of the image containing the template region to the coordinate value of the image containing the reference region so as to match the corresponding points with each other, effecting first affine conversion including at least rotation and movement correction and enlargement or reduction correction on the image containing the template region using the thus determined coefficient, again effecting template matching on the plurality of images which have been subjected to the first affine conversion to determine a coefficient of affine conversion, and effecting second affine conversion on the image containing the template region using the thus determined coefficient to effect rotation and movement correction and enlargement or reduction correction.

According to this method, since at least two regions of interest are defined in a plurality of images to be superimposed and template matching and affine conversion are effected using the regions of interest to align the plurality of images, it is possible to more quickly and accurately align a plurality of images than in the case where template matching and affine conversion are effected on the entire images to align the plurality of images.

However, since template matching for matching the template region with the reference region is effected without correction in this method, in the case where the template region is considerably rotated or enlarged or reduced with respect to the reference region, the accuracy of template matching may be reduced, whereby the plurality of images cannot be aligned in a desired manner even if affine conversion is effected.

Further, even in this method, since it is necessary to effect template matching by obtaining correlation between all pixels within the two regions of interest, calculation time cannot sufficiently be shortened. For solving the latter problem and shortening calculation time required for template matching, Japanese Patent Application Laid Open No. 63-211474 proposes a template matching method comprising the steps of effecting template matching stepwise, determining in each step a point where the degree of correlation is highest, and effecting template matching by reducing a template region based on the thus determined point so that the data quantity to be processed is constant.

However, in the case where template matching is effected as the template region is reduced step by step, if a point where the degree of correlation is highest is erroneously determined in a certain step, template matching cannot be accurately effected.

SUMMARY OF THE INVENTION

It is therefore an object of the present invention to provide an image processing apparatus which can accurately correct the deviation in position between images.

It is another object of the present invention is to provide an image processing apparatus which can accurately effect template matching within a short time period.

The above objects of the present invention can be accomplished by an image processing apparatus comprising temporary memory means for two-dimensionally mapping and temporarily storing image data containing image data regions corresponding to at least two image regions having similar shape and stored in image data storing means, display means for reproducing an image based on the image data stored in the temporary memory means, pixel specifying means for specifying pixels corresponding to at least two equivalent points in at least two image regions having similar shape in the image displayed on the display means, data correcting means for effecting, between micro region image data corresponding to micro regions including coordinates of the at least two pixels specified by the pixel specifying means as center coordinates, rotation and movement correction and enlargement/reduction magnification correction on the micro region image data in the image data corresponding to one image region so that a rotation angle and an enlargement/reduction magnification of the one image region coincide with those of a reference image region which is one of the at least two image regions, template matching means for effecting template matching on the micro region image data corrected by the data correcting means and the micro region image data in the image data corresponding to the reference image region, and affine converting means for effecting affine conversion on the image data stored in the temporary memory means based on the result of the template matching effected by the template matching means.

In a preferred aspect of the present invention, the image processing apparatus further comprises inter-image calculating means for effecting inter-image calculation processing on the image data which have been subjected to affine conversion and the image data corresponding to the reference image region.

In a further preferred aspect of the present invention, the image data are image data produced from the same object under different conditions.

Another object of the present invention can be accomplished by an image processing apparatus comprising temporary memory means for two-dimensionally mapping and temporarily storing image data containing image data regions corresponding to at least two image regions having similar shape and stored in image data storing means, display means for reproducing an image based on the image data stored in the temporary memory means, pixel specifying means for specifying pixels corresponding to at least two equivalent points in at least two image regions having similar shape in the image displayed on the display means, and template matching means for effecting template matching between micro region image data corresponding to micro regions including coordinates of the at least two pixels specified by the pixel specifying means as center coordinates, the template matching means being constituted so as to effect template matching in a plurality steps within a region including as a center pixel a pixel whose degree of correlation was determined to be highest one step earlier while step by step reducing the number of pixels to be subtracted from image data in a template region, pixel intervals between which correlation is to be calculated and the size of the region of pixels from which correlation is to be calculated.

In a preferred aspect of the present invention, the template matching means is constituted so as to select a predetermined number of pixels in order from the pixel whose correlation is highest in each step except a final step and determine a pixel whose correlation is highest.

In a further preferred aspect of the present invention, the pixel specifying means is constituted so as to specify pixels corresponding to at least two equivalent points in at least two image regions having similar shape in the image displayed on the display means and the image processing apparatus further comprises data correcting means for effecting rotation and movement correction and enlargement/reduction magnification correction on the micro region image data in the image data corresponding to one image region so that a rotation angle and an enlargement/reduction magnification of the one image region coincide with those of a reference image region which is one of the at least two image regions and affine converting means for effecting affine conversion on the image data stored in the temporary memory means based on the result of the template matching effected by the template matching means, the template matching means being constituted so as to effect template matching on the micro region image data corrected by the data correcting means and the micro region image data in the image data corresponding to the reference image region.

In a further preferred aspect of the present invention, the image processing apparatus further comprises a subtraction processing section for effecting subtraction processing on image data which have been subjected to affine conversion and image data corresponding to the reference image region.

In a further preferred aspect of the present invention, the image data are image data produced from the same object under different conditions.

In a further preferred aspect of the present invention, the image data are produced using a stimulable phosphor sheet.

In a further preferred aspect of the present invention, the image data are constituted by image data selected from a group consisting of radiation image data of an object, autoradiographic image data, radiographic diffraction image data, electron microscopic image data and chemiluminescent image data.

In a further preferred aspect of the present invention, the radiation image data of the object, the autoradiographic image data, the radiographic diffraction image data and the electron microscopic image data are produced by absorbing and storing the energy of a radiation or an electron beam emitted from a specimen in a stimulable phosphor, irradiating the stimulable phosphor with an electromagnetic wave and photoelectrically converting light emitted from the stimulable phosphor.

In a further preferred aspect of the present invention, the chemiluminescent image data are produced by absorbing and storing the energy of a visible light emitted from a specimen in a stimulable phosphor, irradiating the stimulable phosphor with an electromagnetic wave and photoelectrically converting light emitted from the stimulable phosphor.

In the present invention, the stimulable phosphor employed for producing radiation image data of the object, autoradiographic image data, radiographic diffraction image data and an electron microscopic image data may be of any type insofar as it can store radiation energy or electron beam energy and can be stimulated by an electromagnetic wave to release the radiation energy or electron beam energy stored therein in the form of light. However, a stimulable phosphor which can be stimulated by light having a visible light wavelength is preferably employed. More specifically, preferably employed stimulable phosphors include alkaline earth metal fluorohalide phosphors $(Ba_{1-x}M^{2+}_x)FX:yA$ (where $M^{2+}$ is at least one alkaline earth metal selected from the group consisting of Mg, Ca, Sr, Zn and Cd; X is at least one halogen selected from the group consisting of Cl, Br and I, A is at least one element selected from the group consisting of Eu, Tb, Ce, Tm, Dy, Pr, He, Nd, Yb and Er; x is equal to or greater than 0 and equal to or less than 0.6 and y is equal to or greater than 0 and equal to or less than 0.2) disclosed in U.S. Pat. No. 4,239,968, alkaline earth metal fluorohalide phosphors SrFX:Z (where X is at least one halogen selected from the group consisting of Cl, Br and I; and Z is at least one of Eu and Ce) disclosed in Japanese Patent Application Laid Open No. 2-276997, europium activated complex halide phosphors BaFX xNaX':aEu$^{2+}$ (where each of X and X' is at least one halogen selected from the group consisting of Cl, Br and I; x is greater than 0 and equal to or less than 2; and y is greater than 0 and equal to or less than 0.2) disclosed in Japanese Patent Application Laid Open No. 59-56479, cerium activated trivalent metal oxyhalide phosphors MOX:xCe (where M is at least one trivalent metal selected from the group consisting of Pr, Nd, Pm, Sm, Eu, Tb, Dy, Ho, Er, Tm, Yb and Bi; X is at least one halogen selected from the group consisting of Br and I; and x is greater than 0 and less than 0.1) disclosed in Japanese Patent Application Laid Open No. 58-69281, cerium activated rare earth oxyhalide phosphors LnOX:xCe (where Ln is at least one rare earth element selected from the group consisting of Y, La, Gd and Lu; X is at least one halogen selected from the group consisting of Cl, Br, and I; and x is greater than 0 and equal to or less than 0.1) disclosed in U.S. Pat. No. 4,539,137 and europium activated complex halide phosphors $M^{II}FX$ $aM^{I}X'$ $bM^{III}X''_2$ $cM^{III}X'''_3$ xA:yEu$^{2+}$ (where $M^{II}$ is at least one alkaline earth metal selected from the group consisting of Be, Sr and Ca; $M^{I}$ is at least one alkaline metal selected from the group consisting of Li, Na, K, Rb and Cs; $M^{II}$ is at least one divalent metal selected from the group consisting of Be and Mg; $M^{III}$ is at least one trivalent metal selected from the group consisting of Al, Ga, In and Tl; A is at least one metal oxide; X is at least one halogen selected from the group consisting of Cl, Br and I; each of X', X" and X''' is at least one halogen selected from the group consisting of F, Cl, Br and I; a is equal to or greater than 0 and equal to or less than 2; b is equal to or greater than 0 and equal to or less than $10^{-2}$; c is equal to or greater than 0 and equal to or less than $10^{-2}$; a+b+c is equal to or greater than $10^{-2}$; x is greater than 0 and equal to or less than 0.5; and y is greater than 0 and equal to or less than 0.2) disclosed in U.S. Pat. No. 4,962,047.

In the present invention, the stimulable phosphor employed for producing a chemiluminescent image may be of any type insofar as it can store the energy of light having a visible light wavelength and can be stimulated by an electromagnetic wave to release the energy of light having a visible light wavelength stored therein in the form of light. However, a stimulable phosphor which can be stimulated by light having a visible light wavelength is preferably employed. More specifically, preferably employed stimulable phosphors include metal halophosphates, rare-earth-activated phosphors, aluminate-host phosphors, silicate-host phosphors and fluoride-host phosphors disclosed in UK Patent Application 2,246,197 A.

The above and other objects and features of the present invention will become apparent from the following description made with reference to the accompanying drawings.

DESCRIPTION OF THE PREFERRED EMBODIMENTS

Figure 1:
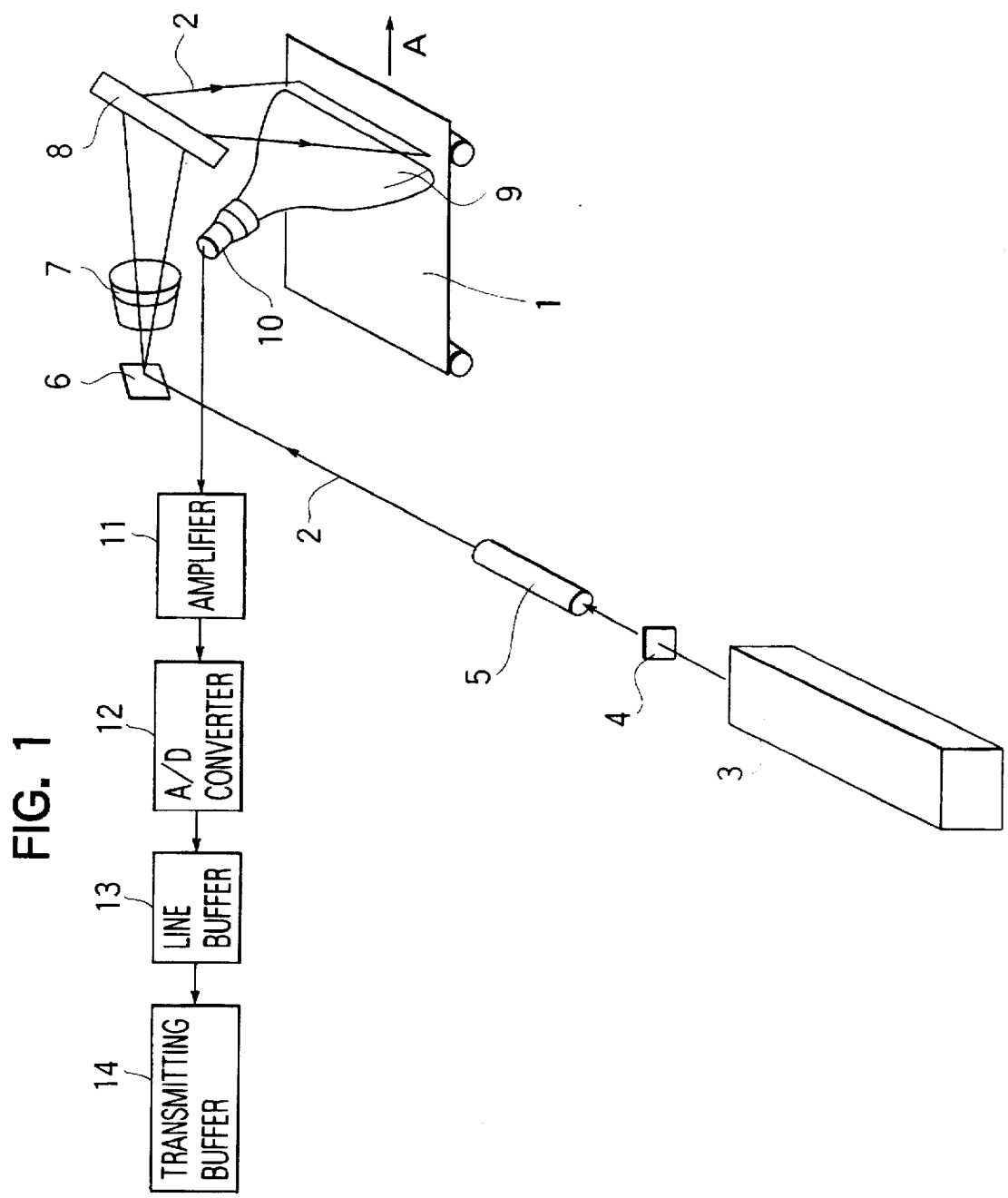
FIG. 1 is a schematic perspective view showing one example of an image reading apparatus for producing image data to be processed by an image processing apparatus which is an embodiment of the present invention.

FIG. 1 is a schematic perspective view showing one example of an image reading apparatus for producing image data to be processed by an image processing apparatus which is an embodiment of the present invention.

A stimulable phosphor sheet 1 shown in FIG. 1 stores locational information regarding a radioactively labeled substance contained in an encephalon slice (not shown) of a test mouse gathered when a first predetermined time period, for example, one hour has passed after drug labeled with a radioactively labeled substance was introduced into the test mouse.

Locational information as termed here includes a variety of information relating to the location of radioactive labeled substances, or aggregations thereof, present in a specimen, such as the location, the shape, the concentration, the distribution or combinations thereof.

The stimulable phosphor sheet which stores the locational information regarding a radioactively labeled substance is scanned with a laser beam 2 and stimulated, thereby being caused to emit stimulated emission.

The laser beam 2 is generated by a laser beam source 3 and passes through a filter 4 to cut off light in the wavelength region corresponding to the wavelength region of stimulated emission to be emitted from the stimulable phosphor sheet 1 in response to stimulation by the laser beam 2. The beam diameter of the laser beam 2 is accurately adjusted by a beam expander 5 and the laser beam 2 enters a beam deflector 6 such as a galvanometer. The laser beam 2 deflected by the beam deflector 6 passes through an fθ lens 7 and is reflected by a plane reflecting mirror 8, thereby impinging upon the stimulable phosphor sheet 1. The fθ lens 7 ensures that the stimulable phosphor sheet 1 is always scanned with the laser beam 2 at a uniform beam speed.

The stimulable phosphor sheet 1 is conveyed in the direction along the arrow A in FIG. 1 in synchronism with the above mentioned scanning with the laser beam 2 so that the whole surface of the stimulable phosphor sheet 1 is scanned by the laser beam 2.

When irradiated with the laser beam 2, the stimulable phosphor sheet 1 releases stimulated emission in an amount proportional to the radiation energy stored therein and the stimulated emission enters a light guiding sheet 9.

The light receiving end of the light guiding sheet 9 has a linear shape and is positioned in the vicinity of the stimulable phosphor sheet 1 so as to face the scanning line on the stimulable phosphor sheet 1. The exit end of the light guiding sheet 9 is in the form of a ring and is connected to the light receiving surface of a light detector 10 such as a photomultiplier for photoelectrically detecting light. This light guiding sheet 9 is made by processing a transparent thermoplastic resin sheet such as an acrylic synthetic resin and so constituted that the emission introduced from the light receiving end is transmitted to the exit end under repeated total reflection within the light guiding sheet 9 and received by the light receiving surface of the light detector 10 via the exit end.

Therefore, the stimulated emission produced by the stimulable phosphor sheet 1 upon being irradiated with the laser beam 2 enters into the light guiding sheet 9 and is received by the light detector 10 via the exit end under repeated total reflection within the sheet 9.

On the light receiving surface of the light detector 10 is provided a filter which allows only light of the wavelength region of the stimulated emission released from the stimulable phosphor sheet 1 to pass through and cuts off light of the wavelength region of the laser beam so that the light detector 10 can photoelectrically detect only the stimulated emission released from the stimulable phosphor sheet 1.

The stimulated emission photoelectrically detected by the light detector 10 is converted to an electrical signal, amplified by an amplifier 11 having a predetermined amplifying factor so as to produce an electrical signal of a predetermined level and then input to an A/D converter 12. The electrical signal is converted to a digital signal with a scale factor suitable for the signal fluctuation width and input to a line buffer 13. The line buffer 13 temporarily stores image data corresponding to one scanning line. When the image data corresponding to one scanning line have been stored in the line buffer 13 in the above described manner, the line buffer 13 outputs the data to a transmitting buffer 14 whose capacity is greater than that of the line buffer 13 and when the transmitting buffer 15 has stored a predetermined amount of the image data, it outputs the image data to an autoradiographic image analyzing apparatus.

Figure 2:
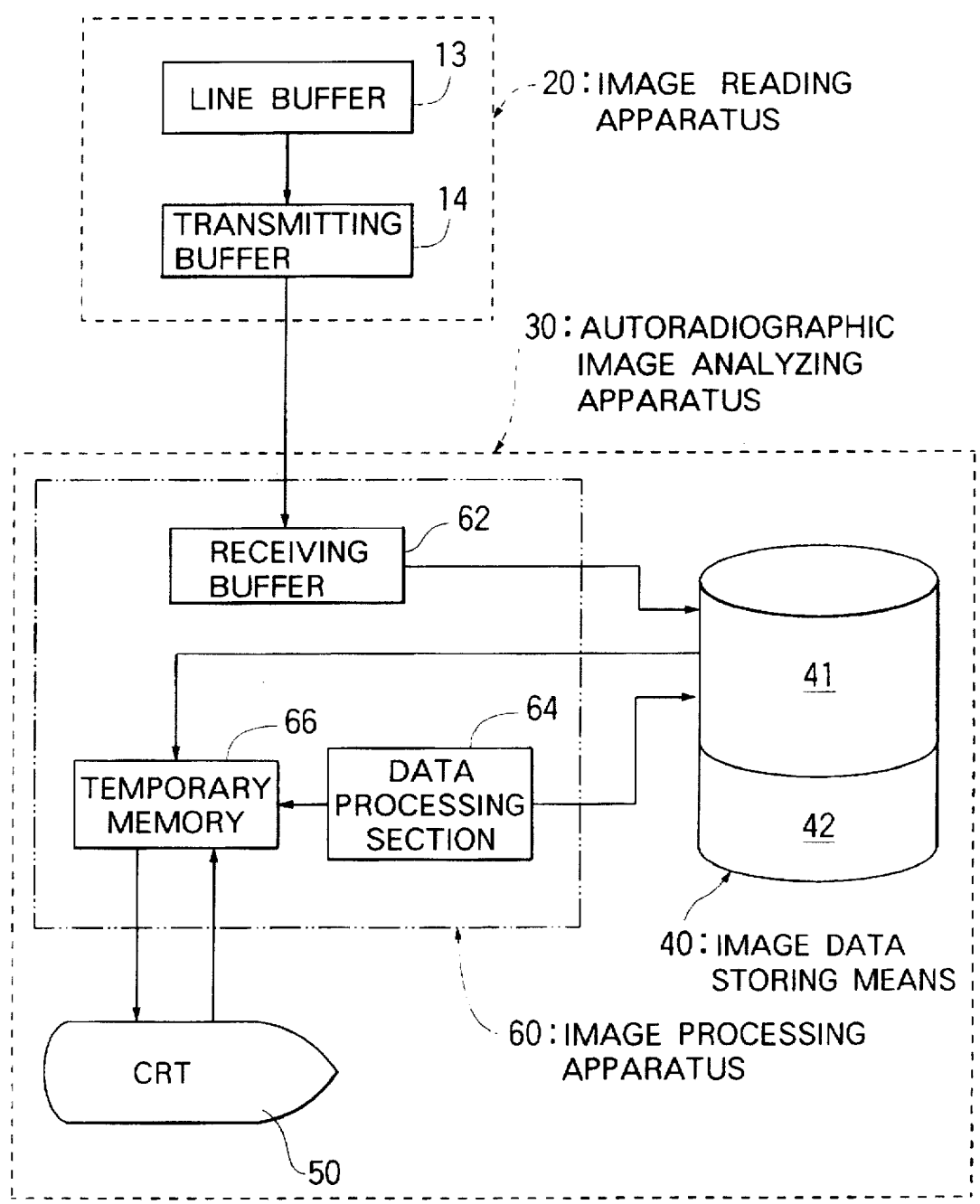
FIG. 2 is a block diagram of an autoradiographic image analyzing apparatus including an image processing apparatus which is an embodiment of the present invention and an image reading apparatus.

FIG. 2 is a block diagram of an autoradiographic image analyzing apparatus including an image processing apparatus which is an embodiment of the present invention and the image reading apparatus.

As shown in FIG. 2, the autoradiographic image analyzing apparatus 30 includes an image processing apparatus 60 for receiving image data containing locational information regarding a radioactively labeled substance contained in a specimen, which were stored and recorded in the stimulable phosphor sheet 1, read out by the image reading apparatus 20 and converted to a digital signal, and processing them so as to reproduce a visible image which has desirable density, tone, contrast and the like, and has excellent observation and analysis property, image data storing means 40 for storing image data which were input to the image processing apparatus 60 from the image reading apparatus 20, and a CRT 50 for reproducing an image based on the image data containing locational information regarding a radioactively labeled substance contained in a specimen.

The image data temporarily stored in the transmitting buffer 14 of the image reading apparatus 20 are input to a receiving buffer 62 in the image processing apparatus 60 of the autoradiographic image analyzing apparatus 30 and temporarily stored therein. When a predetermined amount of the image data have been stored in the receiving buffer 62, the stored image data are output to an image data temporary storing section 41 in the image data storing means 40 and stored therein. In this manner, the image data fed from the transmitting buffer 14 of the image reading apparatus 20 to the receiving buffer 62 of the image processing apparatus 60 and temporarily stored therein are further fed from the receiving buffer 62 to the image data temporary storing section 41 in the image data storing means 40 and stored therein. When the image data obtained by scanning the whole surface of the stimulable phosphor sheet 1 with the laser beam 2 have been stored in the image data temporary storing section 41 in the image data storing means 40, a data processing section 64 in the image processing apparatus 60 reads the image data from the image data temporary storing section 41 and stores them in a temporary memory 66 of the image processing apparatus 60 and after the image data have been subjected to required signal processing, it stores only them in an image data storing section 42 in the image data storing means 40. Then, the image data stored in the image data temporary storing section 41 are discarded.

Similarly to the above, the stimulable phosphor sheet 1 which stores locational information regarding a radioactively labeled substance contained in an encephalon slice (not shown) of a test mouse gathered when a second predetermined time period, for example, two hours have passed after drug labeled with a radioactively labeled substance was introduced into the test mouse is scanned with the laser beam 2 to produce image data and the image data are stored in the image data storing section 42 of the image data storing means 40.

Image data stored in the image data storing section 42 of the image data storing means 40 are read by the data processing section 64 and an image is displayed on the screen of the CRT 50 so that an operator can view and analyze it.

Figure 3:
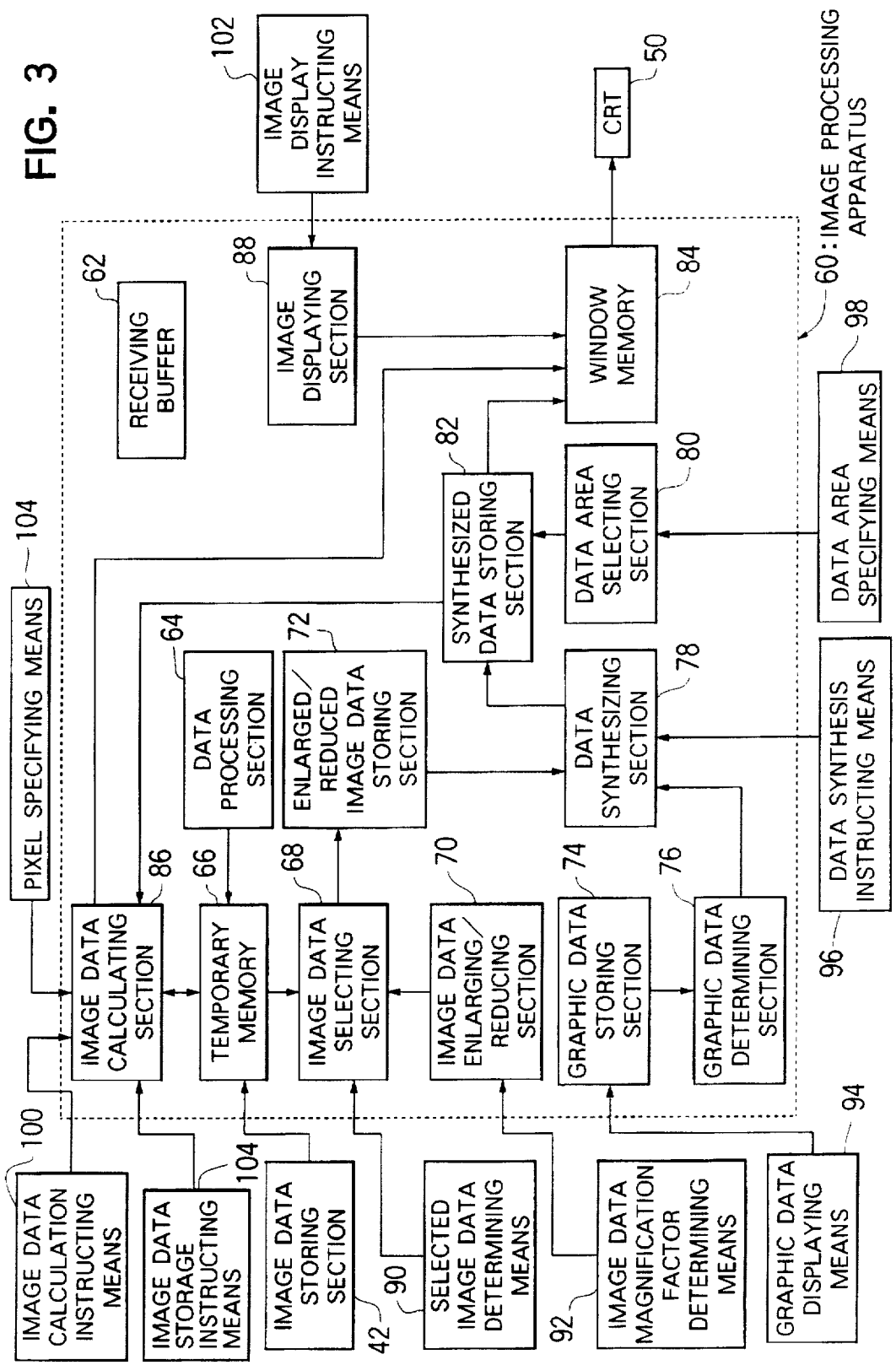
FIG. 3 is a block diagram of an image processing apparatus which is an embodiment of the present invention.

FIG. 3 is a block diagram of the image processing apparatus 60. As shown in FIG. 3, the image processing apparatus 60 includes the receiving buffer 62 for receiving the image data from the transmitting buffer 14 of the image reading apparatus 20, the data processing section 64 for effecting data processing, and the temporary memory 66 for temporarily storing the image data. The temporary memory 66 is constituted so as to two-dimensionally map and temporarily store the image data and has a capacity which can two-dimensionally map and temporarily store image data read from a plurality of stimulable sheets 1.

The image processing apparatus 60 further includes an image data selecting section 68 for selecting a part of image data from among the image data temporarily stored in the temporary memory 66, an image data enlarging/reducing section 70 for enlarging or reducing the image data selected by the image data selecting section 68, an enlarged/reduced image data storing section 72 for two-dimensionally mapping and temporarily storing the image data enlarged or reduced by the image data enlarging/reducing section 70, a graphic data determining section 76 for selecting predetermined graphic data from among the graphic data stored in a graphic data storing section 74 and determining a position and size of a figure in order to superimpose them on the image data two-dimensionally mapped and temporarily stored in the enlarged/reduced image data storing section 72, a data synthesizing section 78 for synthesizing the image data temporarily stored in the image data enlarging/reducing section 70 and the graphic data selected by the graphic data determining section 76 and to be displayed on the screen of the CRT 50, a synthesized image data storing section 80 for two-dimensionally mapping and temporarily storing the image data and the graphic data synthesized by the data synthesizing section 78, a data area selecting section 82 for selecting a predetermined data area from among the image data and the graphic data temporarily stored in the synthesized image data storing section 82, a window memory 84 for two-dimensionally mapping and temporarily storing the data in the data area of the image data and graphic data selected by the data area selecting section 80, an image data calculating section 86 for effecting calculation processing on the image data stored in the window memory, and an image displaying section 88 for producing an image on the screen of the CRT 50 based on the image data and the graphic data two-dimensionally mapped and temporarily stored in the window memory 84.

An image data selecting signal is input to the image data selecting section 68 from a selected image data determining section 90 and an enlarging/reducing signal is input to the image data enlarging/reducing section 70 from an image data magnification factor determining section 92. Further, a graphic data displaying signal is input to the graphic data determining section 76 from graphic data displaying means 94 and a data synthesizing signal is input to the data synthesizing section 78 from data synthesis instructing means 96 which determines what graphic data should be selected and how the image data and the graphic data are to be synthesized to be displayed on the screen of the CRT 50. Moreover, a data area specifying signal is input to the data area selecting section 80 from data area specifying means 98 and an image displaying signal is input to the image data displaying section 88 from image display instructing means 102. Further, an image data calculation signal is input to the image data calculating section 86 from an image data calculation instructing means 100 and a pixel specifying signal is input thereto from a pixel specifying means 104.

In this embodiment, the selected image data determining section 90, the image data magnification factor determining section 92, the graphic data displaying means 94, the data synthesis instructing means 96, the data area specifying means 98, the image display instructing means 102, the image data calculation instructing means 100 and the pixel specifying means 104 can be operated by a mouse (not shown).

The thus constituted image analyzing apparatus 30 defines a region of interest in an image on the screen of the CRT 50 based on image data stored in the image data storing means 40 and graphic data stored in the graphic data storing section 74 in the following manner.

Image data stored in the image data storing means 40 are first two-dimensionally mapped and stored in the temporary memory 66. The selected image data determining section 90 is then operated and a part of the image data two-dimensionally mapped and stored in the temporary memory 66 is selected to be two-dimensionally mapped and stored in the image data selecting section 68. The image data two-dimensionally mapped and stored in the image data selecting section 68 are then two-dimensionally mapped and stored in the enlarged/reduced image data storing section 72 without being enlarged or reduced and are further two-dimensionally mapped and stored in the synthesized image data storing section 82 without synthesizing graphic data therewith. The image data two-dimensionally mapped and stored in the synthesized image data storing section 82 are two-dimensionally mapped and stored in the window memory 84 and when the image display instructing means 102 is operated, an image is formed on the screen of the CRT 50.

An operator views the image displayed on the screen of the CRT 50 and, as occasion demands, operates the image data magnification factor determining section 92 so as to cause the image data enlarging/reducing section 70 to enlarge or reduce the image data two-dimensionally mapped and stored in the image data selecting section 68 and two-dimensionally map and store them in the enlarged/reduced image data storing section 72. The image data two-dimensionally mapped and stored in the enlarged/reduced image data storing section 72 are then read by the data synthesizing section 78 and two-dimensionally mapped and stored in the synthesized image data storing section 82. When the operator specifies a part of the area in the image data two-dimensionally mapped and stored in the synthesized image data storing section 82 by operating the data area specifying means 98, the specified image data are output to the window memory 84 and are two-dimensionally mapped and stored therein. When the image display instructing means 102 is operated, an image is formed on the screen of the CRT 50 by the image displaying section 86 based on the image data two-dimensionally mapped and stored in the window memory 84.

Figure 4:
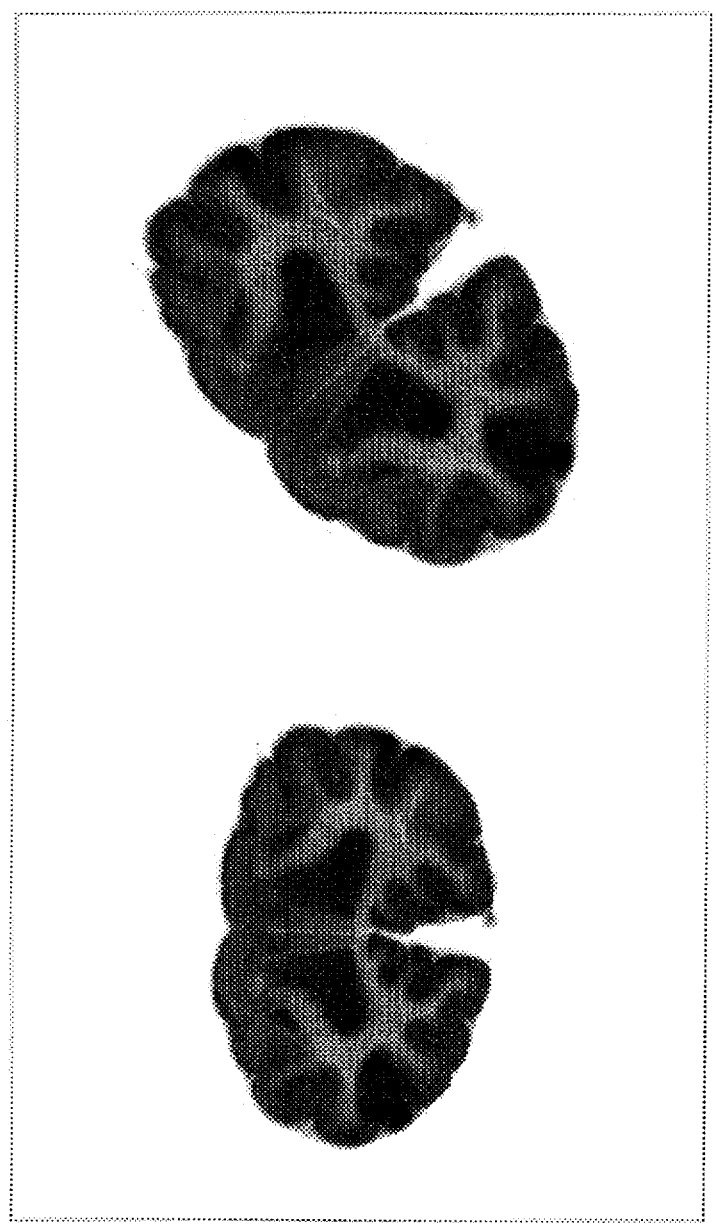
FIG. 4 is a half tone image showing an autoradiographic image of a radioactively labeled substance in an encephalon slice of a test mouse displayed on a screen of a CRT.

FIG. 4 shows the autoradiographic image of a radioactively labeled substance of an encephalon slice of a test mouse. FIG. 4 shows examples of two images of the encephalon slice displayed on the screen of the CRT 50 based on the image data selected by the selected image data determining section 90 and the data area specifying means 98 from among the image data produced by reading from the stimulable phosphor sheet 1 storing in the form of radiation energy locational information of a radioactively labeled substance contained in the encephalon slice of the test mouse gathered when a first predetermined time period, for example, one hour has passed after drug was introduced into the test mouse and the stimulable phosphor sheet 1 storing in the form of radiation energy locational information of a radioactively labeled substance contained in the encephalon slice of the test mouse gathered when a second predetermined time period, for example, two hours have passed after the drug was introduced into the test mouse and stored in the image data storing section 42.

As shown in FIG. 4, since the two images displayed on the screen of the CRT 50 show locational information of a radioactively labeled substance contained in the encephalon slice of the test mouse gathered when a first predetermined time period has passed after the drug was introduced into the test mouse and locational information of a radioactively labeled substance contained in the encephalon slice of the test mouse gathered when a second predetermined time period has passed after the drug was introduced into the test mouse, they contain image regions having the same shape. In the case of analyzing these images, in order to examine, for example, what amount of drug has accumulated at a predetermined portion of the encephalon of the test mouse during the time period from the first predetermined time to the second predetermined time, subtraction processing is sometimes effected by superimposing corresponding image regions and subtracting the density level of each pixel constituting the image data within one of the image regions from that of each pixel constituting the image data within the other the image region.

This embodiment is therefore configured to enable definition of image regions to be superimposed in the two image regions.

The operator selects a figure for defining an image region displayed on the screen of the CRT 50 whose density is to be obtained by drawing the figure on the screen of the CRT 50 using a mouse (not shown). More specifically, when the operator requests synthesis of image data and graphic data in advance by operating the data synthesis instructing means 96 and operates the graphic data displaying means 94 by operating the mouse, a graphic data displaying signal containing locational information produced in accordance with the operation of the mouse is input to the graphic data determining section 76. The graphic data corresponding to the locational information are read from the graphic data storing section 74 by the graphic data determining section 76 to the data synthesizing section 78 and are synthesized with the image data two-dimensionally mapped and stored in the enlarged/reduced image data storing section 72. The synthesized image data and graphic data are two-dimensionally mapped and stored in the synthesized image data storing section 82 and a figure is displayed on the image displayed on the screen of the CRT 50 via the window memory 84. As a result, a predetermined image region is defined by the figure in the image displayed on the CRT 50. The coordinate values of the image data and the graphic data two-dimensionally mapped and stored in the synthesized image data storing section 82 are input to the image data calculating section 86.

Figure 5:
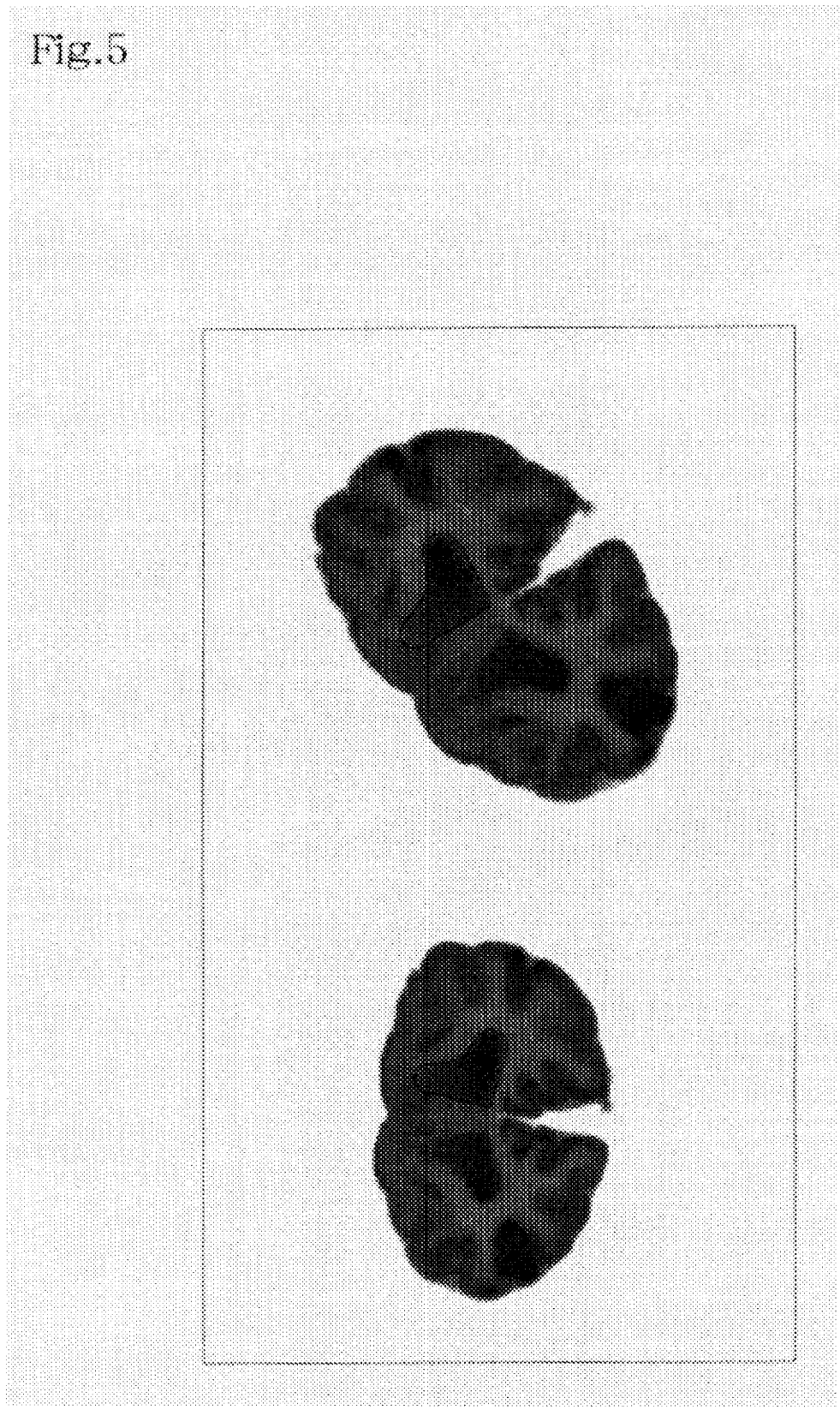
FIG. 5 is a half tone image showing a screen of a CRT in which corresponding image regions in two images are defined as regions of interest by figures.

FIG. 5 shows two corresponding image regions in two images displayed on the screen of the CRT 50 defined by figures as regions of interest.

However, in the examples shown in FIGS. 4 and 5, the orientations of the encephalon slices are different from each other because when the encephalon slices of the test mouse were superimposed on the stimulable phosphor sheet 1 and the stimulable phosphor sheet 1 was exposed, the image regions were not in the same orientation and, therefore, the image regions are rotated with respect to each other. Moreover, since the regions of the image data selected by the selected image data determining section 90 and the data area specifying means 98 are different from each other, the positions of the image regions in the images are different from each other. Further, since the magnification factors of enlargement/reduction effected by the image data enlarging/reducing section 70 are different from each other, the size of the image regions are different from each other. Therefore, it is impossible to superimpose the two images as they are.

Therefore, in this embodiment, in the case where two corresponding regions of interest in two images displayed on the screen of the CRT 50 are superimposed, the operator, after having used the mouse and operated the image data calculation instructing means 100, specifies two pairs of points, one pair in each of the two regions of interest, which can be considered to correspond to each other, using the mouse while viewing the two corresponding regions of interest in the two images displayed on the screen of the CRT 50. As a result, the pixel specifying means 104 is operated and an image data calculation signal is input to the image date calculating section 86. The image date calculating section 86 accesses the temporary memory 66 and reads the coordinate values of the two points specified by the operator from the two sets of image data two-dimensionally mapped and temporarily stored in the temporary memory 66.

Figure 6:
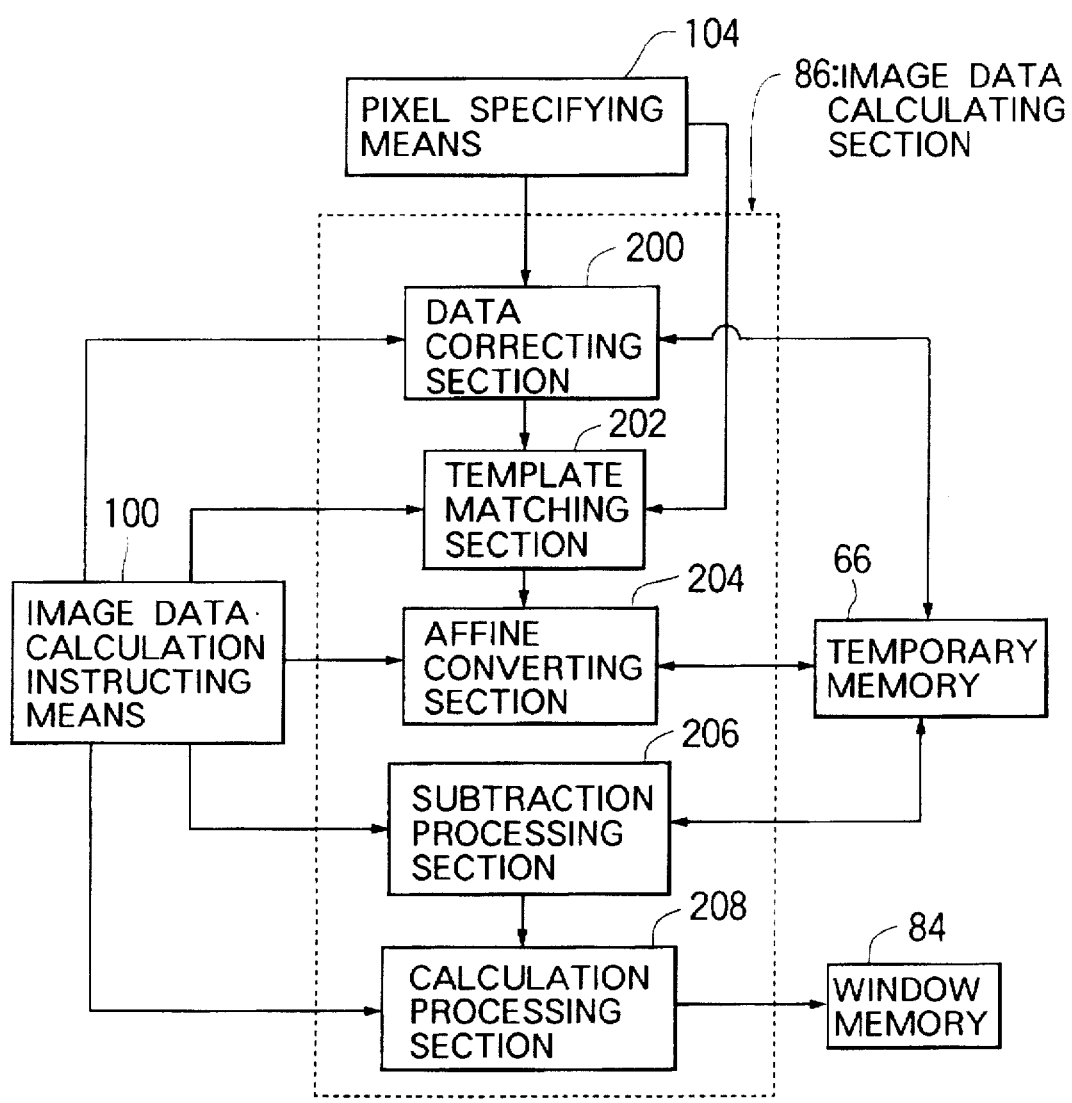
FIG. 6 is a block diagram of an image data calculating section.

FIG. 6 is a block diagram of the image date calculating section 86.

As shown in FIG. 6, the image date calculating section 86 includes a data correcting section 200 for reading two sets of image data stored in the temporary memory 66, calculating the deviation between the two sets of image data and correcting one of the two sets of image data two-dimensionally mapped and temporarily stored in the temporary memory 66, a template matching section 202 for reading the image data corrected by the data correcting section 200 from the temporary memory 66 and effecting template matching thereon, an affine converting section 204 for effecting affine conversion on the image data corresponding to the region of interest in the one of the image data stored in the temporary memory 66 in accordance with the results of the template matching, a subtraction processing section 206 for reading the image data which correspond to the region of interest and on which affine conversion has been effected and image data corresponding to the region of interest in the other image data, effecting subtraction processing thereon and outputting the image data on which subtraction processing has been effected to the temporary memory 66, thereby causing it to be two-dimensionally mapped and temporarily stored therein, and a calculation processing section 208 for calculating the sum value of density levels of pixels in the region of image data corresponding to the specified region of interest based on the image data on which subtraction processing has been effected, producing table data as occasion demands and outputting them to the window memory 84.

When the pixel specifying means 104 is operated by the operator to specify two pair of points, one pair in each of the two regions of interest, which can be considered to correspond to each other, a pixel specifying signal including locational information of these points is input to the data correcting section 200 and the data correcting section 200 reads the coordinate values of the specified pixels in the image data two-dimensionally mapped and temporarily stored in the temporary memory 66.

Figure 7:
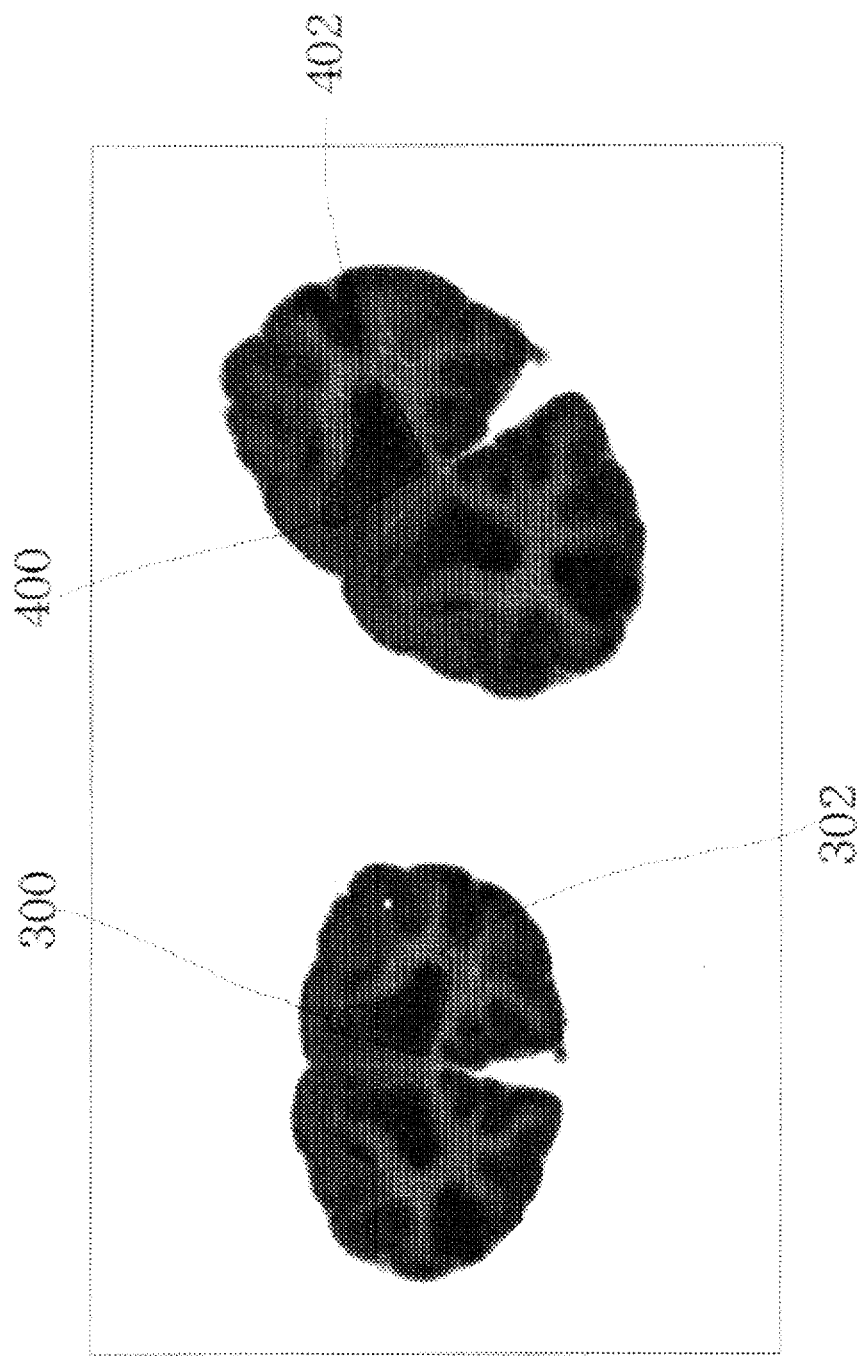
FIG. 7 is a half tone image showing a screen of a CRT in which two pairs of points, one pair in each of two regions of interest are defined, which can be considered to correspond to each other.

FIG. 7 shows the screen of the CRT 50 in which as a result of the operation of the pixel specifying means 104, pairs of points in the regions of interest which can be considered to correspond to each other are specified.

As shown in FIG. 7, since a pair of points 300, 302 and a pair of points 400, 402 are specified by the pixel specifying means 104 in the regions of interest, the difference in the enlargement/reduction magnification factors can be obtained by calculating the lengths of segments of lines based on the coordinate values of the pixels corresponding to the two points 300, 302 and the two points 400, 402 specified in the respective regions of interest and comparing them with each other. Further, it is possible to ascertain how one of the regions of interest is rotated to the other by calculating the angles of the segments of lines each connecting the two points and comparing them. In this embodiment, since the left image in each of FIGS. 4 and 5 is a reference image, the region of interest defined in the right image is superimposed on the region of interest defined in the left image. Therefore, the data correcting section 200 calculates the difference in the enlargement/reduction magnification factors between the region of interest in the right image and that in the left image and how the region of interest in the right image is rotated relative to the region of interest in the left image. For this purpose, the data correcting section 200 corrects image data within a micro template region consisting of a predetermined number of pixels, for example, 200×200 pixels around the pixel corresponding to the point 400 specified by the operator so that the rotation angle and the enlargement/ reduction magnification factor thereof coincide with those of a micro reference region consisting of 200×200 pixels around the pixel corresponding to the point 300 and corrects image data within a micro template region consisting of 200×200 pixels around the pixel corresponding to the point 402 specified by the operator so that the rotation angle and the enlargement/reduction magnification factor thereof coincide with those of a micro reference region consisting of 200×200 pixels around the pixel corresponding to the point 302.

Figure 8:
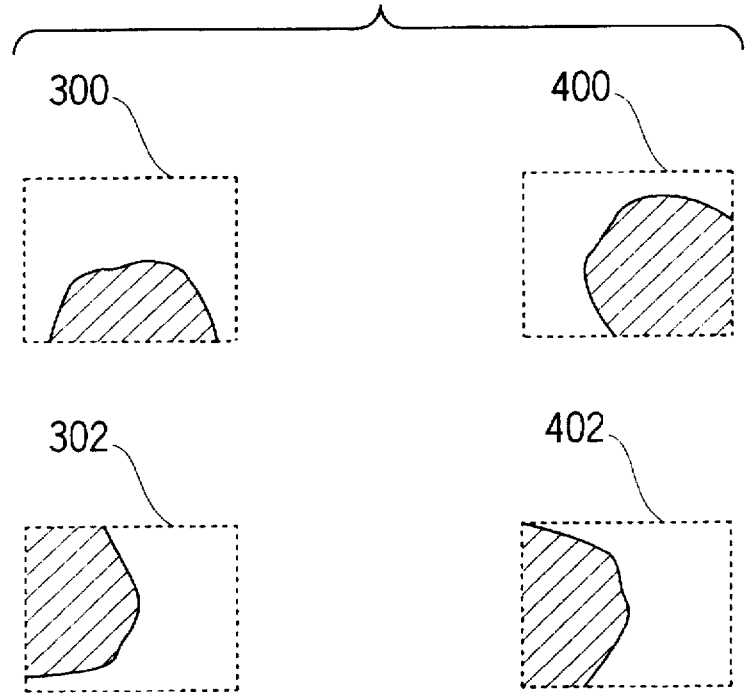
FIG. 8 is a view schematically showing images in a reference region and a template region before correction is made.
Figure 9:
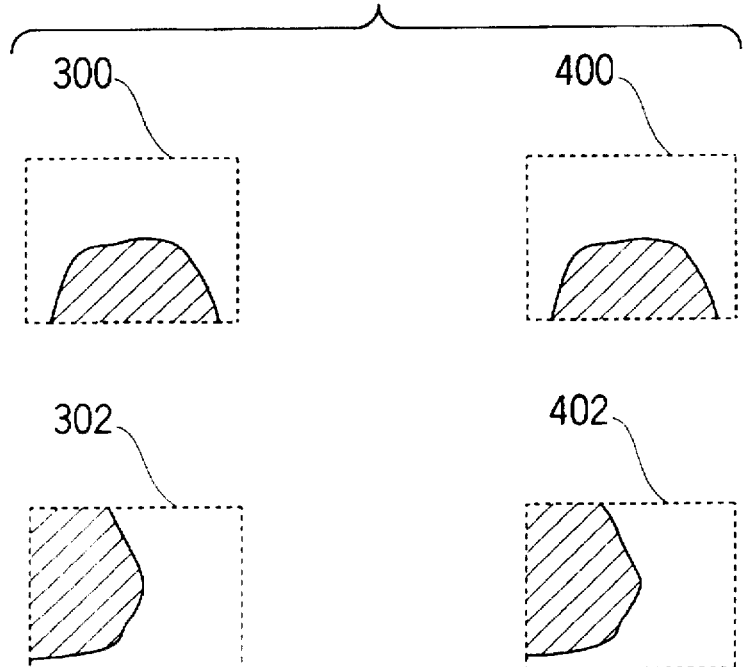
FIG. 9 is a view schematically showing images in a reference region and a template region after correction has been made.

FIG. 8 is a view schematically showing images in a reference region and a template region before correction is made and FIG. 9 is a view schematically showing images in a reference region and a template region after correction has been made. As shown in FIGS. 8 and 9, the data correcting section 200 subjects only the image in the template region to rotation correction and enlargement/reduction.

The image data in the micro template region whose rotation angle and enlargement/reduction magnification factor have been corrected and the image data in the micro reference region are output to the template matching section 202.

The template matching section 202 effects template matching on the image data in the micro template region around the pixel corresponding to the point 400 specified by the operator and the image data in the micro reference region around the pixel corresponding to the point 300 and consisting of the same number of pixels as that in the micro template region and effects template matching on the image data in the micro template region around the pixel corresponding to the point 402 and consisting of the same number of pixels and the image data in the micro reference region around the pixel corresponding to the point 302 and consisting of the same number of pixels.

The template matching section 202 first subtracts seven pixels every eight pixels from the image data in the micro template region consisting of 200×200 pixels to produce a template region and calculates correlation every eight pixels within a region of 64×64 pixels around a predetermined pixel in the micro reference region between the image data in the thus produced template region and the image data in the micro reference region in a well known manner, thereby selecting four pixels in order from the pixel whose correlation value is highest. The template matching section 202 calculates the pixel whose correlation is highest based on the correlation values of these four pixels by the least squares method. The thus obtained pixel whose correlation is highest has an error of ± fourteen pixels.

The template matching section 202 then subtracts three pixels every four pixels from the image data in the micro template region consisting of 200×200 pixels to produce a template region and calculates correlation every four pixels within a region of 29×29 pixels around the pixel whose correlation was determined to be highest one step earlier between the image data in the thus produced template region and the image data in the micro reference region, thereby selecting four pixels in order from the pixel whose correlation value is highest. The template matching section 202 calculates the pixel whose correlation is highest based on the correlation values of these four pixels by the least squares method. The thus obtained pixel whose correlation is highest has an error of ± six pixels.

Therefore, the template matching section 202 subtracts one pixel every two pixels from the image data in the micro template region consisting of 200×200 pixels to produce a template region and calculates correlation every two pixels in a region of 13×13 pixels around the pixel whose correlation was determined to be highest one step earlier between the image data in the thus produced template region and the image data in the micro reference region, thereby selecting four pixels in order from the pixel whose correlation value is highest. The template matching section 202 calculates the pixel whose correlation is highest based on the correlation values of these four pixels by the least squares method. The thus obtained pixel whose correlation is highest has an error of ± two pixels.

Finally, the template matching section 202 calculates correlation within a region of 5×5 around the pixel whose correlation was determined to be highest one step earlier between each pixel in the micro template region consisting of 200×200 pixels and each pixel in the micro reference region, thereby obtaining from the pixel whose correlation value is highest.

For shortening the calculation time required for template matching, two corresponding pairs of pixels are specified and template matching is effected on image data in a predetermined region including the specified pixels based on the correlation method. Generally speaking, the accuracy of the template matching becomes low in the case where, as shown in FIGS. 4 and 5, the enlargement/reduction magnification factor of the template region with respect to the reference region is great and where the rotation angle of the template region with respect to the reference region is great. In particular, since the autoradiographic image is produced by superimposing a specimen and a stimulable phosphor sheet in a darkroom and exposing the stimulable phosphor sheet to radiation and the specimen and the stimulable phosphor sheet cannot be superimposed without fail in a predetermined relationship, the rotation angle of the template region with respect to the reference region is often great. Therefore, the accuracy of the template matching tends to become low. In this embodiment, however, two pairs of points, one pair in each of the two regions of interest, which can be considered to correspond to each other, are specified by the operator and the rotation angle and the enlargement/reduction magnification factor are corrected by the data correcting section 200 based on the coordinate values of the two points specified in each of the two regions of interest, which correspond to those in the other region of interest, whereby the image data in the micro template region is corrected so that the rotation angle and the enlargement/reduction magnification factor thereof substantially correspond to those of the corresponding reference region. Therefore, it is possible to effect template matching by the template matching section 202 with high accuracy.

Further, in the first step, seven pixels are subtracted every eight pixels from the image data in the template region of 200×200 pixels and correlation is calculated every eight pixels within a region of 64×64 pixels around a predetermined pixel in a well known manner, thereby obtaining the pixel whose correlation is highest. In steps after the second step, template matching is effected by gradually reducing the number of pixels to be subtracted from the image data in the micro template region, pixel intervals between which correlation is to be calculated and the size of the region of pixels in which correlation is to be calculated. Therefore, the calculation time required for template matching can be shortened. Further, since correlation is calculated between all pixels in the template region and all pixels in the reference region in the final step and four pixels in order from that having the highest correlation are selected in each step but the final step so that the pixel whose correlation is highest is determined based on the correlation values of the four pixels by the least squares method, the accuracy of template matching can be considerably improved as compared with the case where template matching is effected as the size of the template region is gradually reduced.

As shown in FIGS. 4 and 5, since the image to be superimposed is merely displaced in parallel, rotated and enlarged or reduced with respect to the reference image in this embodiment, it is possible to correct the deviation in position of the image data corresponding to the image to be superimposed with respect to the image data corresponding to the reference image by the following formula.

Formula 1

$$\begin{pmatrix} xa \\ ya \end{pmatrix} = \alpha \begin{pmatrix} \cos\theta & \sin\theta \\ -\sin\theta & \cos\theta \end{pmatrix} \begin{pmatrix} xb \\ yb \end{pmatrix} + \begin{pmatrix} a \\ b \end{pmatrix}$$

wherein xa and ya designate the coordinate values of the reference region, xb and yb designate the coordinate values of the template region, α designates the enlargement/reduction magnification factor of the image region including the template region with respect to the reference region, θ designates the rotation angle of the image region including the template region with respect to the reference region, and a and b designate amounts of parallel displacement of the image region including the template region with respect to the reference region.

The coefficients α, θ, a and b obtained by the template matching effected by the template matching section 202 are output to the affine converting section 204. The affine converting section 204 reads image data containing the template region from among image data two-dimensionally mapped and temporarily stored in the temporary memory 66 and effects affine conversion thereon to output the affine converted image data to the temporary memory 66.

Figure 10:
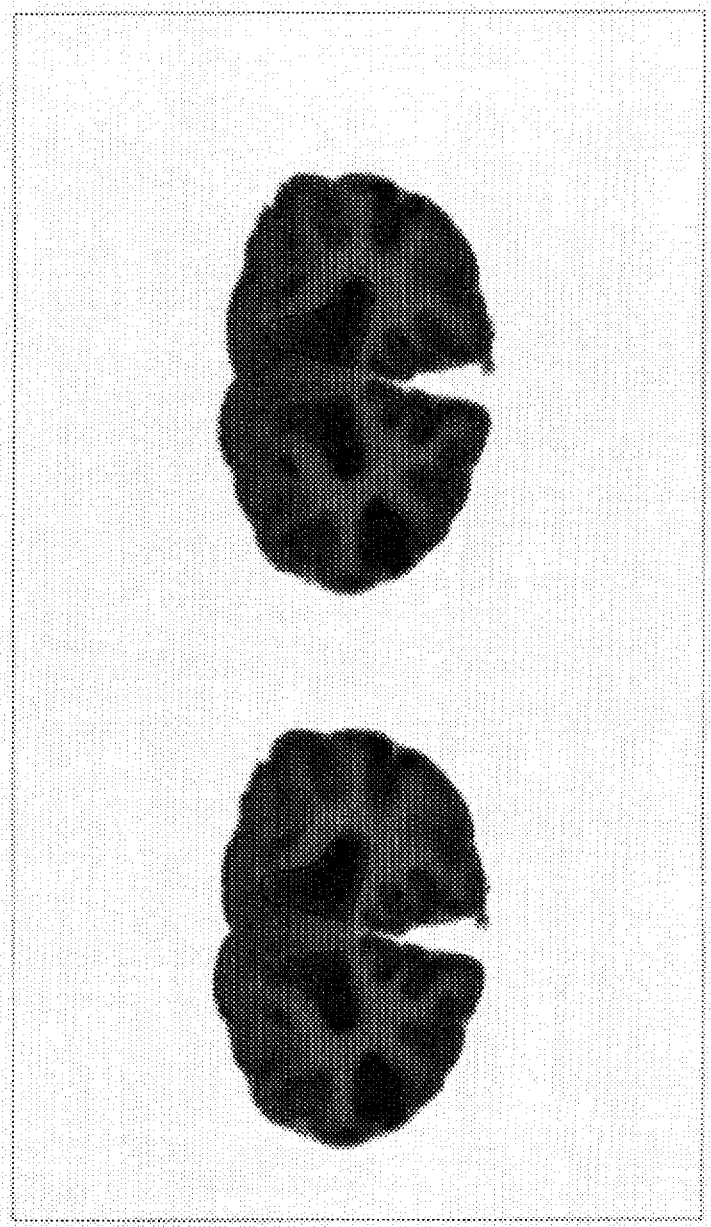
FIG. 10 is a half tone image showing a screen of a CRT after image data containing a template region have been subjected to affine conversion.

As a result, an image is displayed on the screen of the CRT 50 based on the image data which have been subjected to the affine conversion. FIG. 10 shows the screen of the CRT 50 on which the image is displayed based on the thus obtained image data.

Further, when the operator requests to effect subtraction processing by operating the image data calculation instructing means 100, a subtraction effecting signal is input to the subtraction processing section 206. The subtraction processing section 206 reads image data corresponding to the regions of interest from among the two sets of image data two-dimensionally mapped and temporarily stored in the temporary memory 66, effects subtraction processing thereon, two-dimensionally maps and temporarily stores the image data which have been subjected to subtraction processing in a memory area in the temporary memory where no image data are stored and simultaneously outputs them to the calculation processing section 208.

The image data which have been subjected to subtraction processing and two-dimensionally mapped and temporarily stored in the temporary memory 66 are fed to the window memory 84 via the enlarged/reduced image data storing section 72 and the synthesized data storing section 82 and when the image display instructing means 102, an image which have been subjected to subtraction processing is displayed on the screen of the CRT 50 based on the image data.

When an instruction to effect calculation is input from the image data calculation instructing means 100, the calculation processing section 208 calculates the sum value of density levels of pixels in a region of image data corresponding to the specified region of interest based on the image data which have been subjected to subtraction processing and, as occasion demands, produces table data to output them to the window memory 84. When the image display instructing means 102 is operated, the data representing the results of calculation output to the window memory 84 are displayed on the screen of the CRT 50.

According to the above described embodiment, an operator first specifies two pairs of points, one pair in each of two regions of interest, which can be considered to correspond to each other, and after the rotation angle and the enlargement/ reduction magnification factor of the image data including the template region have been corrected based on the coordinate values of the two points in the respective regions of interest, which correspond to the two points in the other region of interest, template matching is effected by the template matching section 202. Therefore, it is possible to improve the accuracy of the template matching and to align two regions of interest in a desired manner.

Further, according to the above described embodiment, since the template matching section 202 effects template matching in four steps within a region around the pixel whose correlation was determined to be highest one step earlier in such a manner that the number of pixels to be subtracted from the image data in the micro template region, pixel intervals between which correlation is to be calculated and the size of the region of pixels in which correlation is to be calculated are gradually reduced, it is possible to complete template matching within a short time period. Moreover, since four pixels in order from that having the highest correlation are selected in each step except the final step so that the pixel whose correlation is highest is determined based on the correlation values of the four pixels by the least squares method, it is possible to effect template matching with high accuracy. Furthermore, according to the above described embodiment, an operator first specifies two pairs of points, one pair in each of two regions of interest, which can be considered to correspond to each other, and after the rotation angle and the enlargement/reduction magnification factor of the image data including the template region have been corrected based on the coordinate values of the two points in the respective regions of interest, which correspond to the two points in the other region of interest, template matching is effected by the template matching section 202. Therefore, template matching can be effected by the template matching section 202 with high accuracy.

The present invention has thus been shown and described with reference to specific embodiments. However, it should be noted that the present invention is in no way limited to the details of the described arrangements but changes and modifications may be made without departing from the scope of the appended claims.

For example, in the above described embodiments, the description is made regarding the case where corresponding regions of interest in an image regarding locational information of a radioactively labeled substance contained in the encephalon slice of a test mouse gathered when the first predetermined time period has passed after a drug was introduced into the test mouse and an image regarding locational information of a radioactively labeled substance contained in the encephalon slice of a test mouse gathered when the second predetermined time period has passed after the drug was introduced into the test mouse are superimposed and subtraction processing is effected thereon. However, the present invention is not limited to such autoradiography but can be applied in any case where it is necessary to superimpose and process image regions between images containing image regions having similar shape. Specifically, the present invention can be widely applied to not only the processing between a plurality of images of the same object but the case where symmetrical image regions are superimposed in an image containing symmetrical image regions such as an image of an encephalon slice and the like. For example, the present invention is applicable to radiation image of an object, a radiographic diffraction image, an electron microscope image, a chemiluminescent image and the like.

Further, in the above described embodiment, although two regions of interest are superimposed and subtraction processing is effected on image data corresponding to the two regions of interest, inter-image calculation processing effected after superimposing the regions of interest is not limited to the subtraction processing but various types of inter-image calculation processing such as superimposing processing can be effected.

Furthermore, in the above described embodiment, although two regions of interest are superimposed, the present invention can be applied to the case where three or more regions of interest are superimposed.

Moreover, in the above described embodiment, since the image containing the template region is merely translated, rotated and enlarged or reduced by a different magnification factor with respect to the reference image, two corresponding pairs of points are specified one pair in each of two regions of interest, and after the rotation correction and the magnification factor correction have been effected on the image data corresponding to the micro template region around the specified points, template matching and affine conversion are effected. However, in the case where a specimen is not correctly in surface contact with the stimulable phosphor sheet 1 when the specimen is superimposed on the stimulable phosphor sheet 1 to expose the stimulable phosphor sheet 1 or the like, when an image containing a template region is warped with respect to the reference image, two steps of three corresponding points are specified one set in each of two regions of interest, and after the rotation correction and the magnification factor correction have been effected on the image data corresponding to the micro template region around the specified points, template matching and affine conversion may be effected.

In this case, affine conversion is effected in accordance with the following formula.

Formula 2

$$\begin{pmatrix} xa \\ ya \end{pmatrix} = \alpha \begin{pmatrix} c & d \\ e & f \end{pmatrix} \begin{pmatrix} xb \\ yb \end{pmatrix} + \begin{pmatrix} a \\ b \end{pmatrix}$$

wherein xa and ya designate the coordinate values of the reference region, xb and yb designate the coordinate values of the template region, and a, b, c, d, e and f are coefficient obtained by template matching.

Further, in the above described embodiment, although the image data are produced by using the stimulable phosphor sheet 1 and converting locational information regarding a radioactively labeled substance to an electrical signal and are displayed on the screen of the CRT 50 as a visible image, it is possible to once form a visible image on a photographic film instead of the stimulable phosphor sheet 1, photoelectrically read the visible image, convert it to an electrical signal and process the thus obtained image data in a similar manner to the above.

Furthermore, although a micro region of 200×200 pixels is used as a template region in the above described embodiment, the size of the template regions can be arbitrarily determined.

Moreover, in the above described embodiment, seven pixels are subtracted every eight pixels from the image data in the micro template region of 200×200 pixels to produce a template region and correlation is calculated every eight pixels within a region of 64×64 pixels around a predetermined pixel between the image data in the micro template region and the image data in the micro reference region to obtain the pixel whose correlation is highest in the first step. This is because the template matching is intended to be completed in four steps and in the final step, correlation is calculated within a region of 5×5 around the pixel whose correlation was determined to be highest one step earlier between each pixel in the micro template region of 200×200 pixels and each pixel in the reference region to obtain the pixel whose correlation is highest. Therefore, it is not absolutely necessary in the first step to subtract seven pixels every eight pixels from the image data in the micro template region of 200×200 pixels to produce a template region and calculate correlation every eight pixels within a region of 64×64 pixels between the image data in the micro template region and the image data in the micro reference region to obtain the pixel whose correlation is highest. More specifically, in the final step, in order to obtain the pixel whose correlation is highest without any error by calculating correlation within a region of 5×5 pixels around the pixel whose correlation was determined to be highest one step earlier between each pixel in the micro template region of 200×200 pixels and each pixel in the reference region, the error in the final step but one has to be ±2 pixels and since one pixel is subtracted every two pixels from the image data in the micro template region of 200×200 pixels to produce a template region and correlation is calculated every two pixels within a region of 13×13 pixels around the pixel whose correlation was determined to be highest one step earlier between the image data in the micro template region and the image data in the micro reference region to obtain the pixel whose correlation is highest, the error in the final step but two has to be ±6 pixels. Further, in the second step three pixels are subtracted every four pixels from the image data in the micro template region of 200×200 pixels to produce a template region and correlation is calculated every four pixels within a region of 29×29 pixels around the pixel whose correlation was determined to be highest one step earlier between the image data in the micro template region and the image data in the micro reference region to obtain the pixel whose correlation is highest. Therefore, since the error one step earlier has to be ±14 pixels, in the first step, seven pixels are subtracted every eight pixels from the image data in the micro template region of 200×200 pixels to produce a template region and correlation is calculated every eight pixels within a region of 64×64 pixels around a predetermined pixel between the image data in the micro template region and the image data in the micro reference region to obtain the pixel whose correlation is highest in the first step. Accordingly, since the number of pixels to be subtracted from the image data in the template region to produce a template region, pixel intervals between which correlation is to be calculated and the size of the region of pixels in which correlation is to be calculated are mathematically determined for eliminating error, the number of pixels to be subtracted from the image data in the template region, pixel intervals between which correlation is to be calculated and the size of the region of pixels in which correlation is to be calculated in the first step depend on the number of steps of the template matching.

Furthermore, in the above described embodiment, although template matching is effected in four steps, the number of steps can be arbitrarily selected depending on the objective image.

Moreover, in the above described embodiment, in the final step, correlation is calculated within a region of 5×5 pixels between each pixel in the micro template region of 200×200 pixels and each pixel in the reference region to obtain the pixel whose correlation is highest. However, since four pixels in order from the pixel having the highest correlation are selected in each step and the pixel whose correlation is highest is obtained based on the correlation values of the thus selected four pixels by the least squares method, the accuracy is markedly improved in each step as compared with the case where only the pixel having the highest correlation value is selected in each step. Therefore, since template matching can be effected with sufficiently high accuracy even if the final step is omitted for shortening the calculation time, the final step may be omitted. Further, depending on the image, even if one or more intermediate steps are omitted, template matching can be effected by effecting the final step and even the final step can be omitted in addition to the omission of one or more intermediate steps.

Furthermore, in the above described embodiment, although four pixels in order from the pixel having the highest correlation are selected and the pixel whose correlation is highest is obtained based on the correlation values of the thus selected four pixels by the least squares method, it is not absolutely necessary to select four pixels in order from the pixel having the highest correlation and a plurality of pixels may be selected in order from the pixel having the highest correlation depending on the image. Further, it is possible to obtain the pixel whose correlation is highest based on a plurality of pixels selected in order from the pixel having the highest correlation by other methods than the least squares method.

Moreover, in the above described embodiment, although template matching is effected after the data correcting section 200 has corrected the rotation angle and the enlargement/reduction of the template region with respect to the reference region, depending on the image, it is not absolutely necessary for the data correcting section 200 to effect correction processing.

Further, in the above described embodiment, although template matching is effected in four steps, template matching may be effected by a well known correlation method to obtain coefficients for affine conversion.

Furthermore, in the present invention, the respective means need not necessarily be physical means and arrangements whereby the functions of the respective means are accomplished by software fall within the scope of the present invention. In addition, the function of a single means may be accomplished by two or more physical means and the functions of two or more means may be accomplished by a single physical means.

According to the present invention, it is possible to provide an image processing apparatus which can accurately effect template matching within a short time period.

We claim:

1. An image processing apparatus comprising temporary memory means for two-dimensionally mapping and temporarily storing image data containing image data regions corresponding to at least two image regions having similar shape and stored in image data storing means, display means for reproducing an image based on the image data stored in the temporary memory means, pixel specifying means for specifying pixels corresponding to at least two-equivalent points in at least two image regions having similar shape in the image displayed on the display means, data correcting means for effecting, between micro region image data corresponding to micro regions including coordinates of the at least two pixels specified by the pixel specifying means as center coordinates, rotation and movement correction and enlargement/reduction magnification correction on the micro region image data in the image data corresponding to one image region so that a rotation angle and an enlargement/reduction magnification of the one image region coincide with those of a reference image region which is one of the at least two image regions, template matching means for effecting template matching on the micro region image data corrected by the data correcting means and the micro region image data in the image data corresponding to the reference image region, and affine converting means for effecting affine conversion on the image data stored in the temporary memory means based on the result of the template matching effected by the template matching means.

2. An image processing apparatus in accordance with claim 1 wherein the image data are image data produced from the same object under different conditions.

3. An image processing apparatus in accordance with claim 1 wherein the image data are produced using a stimulable phosphor sheet and are constituted by image data selected from a group consisting of radiation image data of an object, autoradiographic image data, radiographic diffraction image data, electron microscopic image data and chemiluminescent image data.

4. An image processing apparatus in accordance with claim 1 which further comprises inter-image calculating means for effecting inter-image calculation processing on the image data which have been subjected to affine conversion and the image data corresponding to the reference image region.

5. An image processing apparatus in accordance with claim 4 wherein the image data are image data produced from the same object under different conditions.

6. An image processing apparatus comprising temporary memory means for two-dimensionally mapping and temporarily storing image data containing Image data regions corresponding to at least two image regions having similar shape and stored in image data storing means, display means for reproducing an image based on the image data stored in the temporary memory means, pixel specifying means for specifying pixels corresponding to at least two equivalent points in at least two image regions having similar shape in the image displayed on the display means, and template matching means for effecting template matching between micro region image data corresponding to micro regions including coordinates of the at least two pixels specified by the pixel specifying means as center coordinates, the template matching means being constituted so as to effect template matching in a plurality steps within a region including as a center pixel a pixel whose degree of correlation was determined to be highest one step earlier while step by step reducing the number of pixels to be subtracted from image data in a template region, pixel intervals between which correlation is to be calculated and the size of the region of pixels from which correlation is to be calculated.

7. An image processing apparatus in accordance with claim 6 wherein the image data are image data produced from the same object under different conditions.

8. An image processing apparatus in accordance with claim 6 wherein the image data are produced using a stimulable phosphor sheet and are constituted by image data selected from a group consisting of radiation image data of an object, autoradiographic image data, radiographic diffraction image data, electron microscopic image data and chemiluminescent image data.

9. An image processing apparatus in accordance with claim 6 wherein the template matching means is constituted so as to select a predetermined number of pixels in order from the pixel whose correlation is highest in each step except a final step and determine a pixel whose correlation is highest.

10. An image processing apparatus in accordance with claim 9 wherein the image data are image data produced from the same object under different conditions.

11. An image processing apparatus in accordance with claim 9 wherein the pixel specifying means is constituted so as to specify pixels corresponding to at least two equivalent points in at least two image regions having similar shape in the image displayed on the display means and the image processing apparatus further comprises data correcting means for effecting rotation and movement correction and enlargement/reduction magnification correction on the micro region image data in the image data corresponding to one image region so that a rotation angle and an enlargement/reduction magnification of the one image region coincide with those of a reference image region which is one of the at least two image regions and affine converting means for effecting affine conversion on the image data stored in the temporary memory means based on the result of the template matching effected by the template matching means, the template matching means being constituted so as to effect template matching on the micro region image data corrected by the data correcting means and the micro region image data in the image data corresponding to the reference image region.

12. An image processing apparatus in accordance with claim 11 wherein the image data are image data produced from the same object under different conditions.

13. An image processing apparatus in accordance with claim 11 which further comprises inter-image calculating means for effecting inter-image calculation processing on the image data which have been subjected to affine conversion and the image data corresponding to the reference image region.

14. An image processing apparatus in accordance with claim 13 wherein the image data are image data produced from the same object under different conditions.

15. An image processing apparatus in accordance with claim 6 wherein the pixel specifying means is constituted so as to specify pixels corresponding to at least two equivalent points in at least two image regions having similar shape in the image displayed on the display means and the image processing apparatus further comprises data correcting means for effecting rotation and movement correction and enlargement/reduction magnification correction on the micro region image data in the image data corresponding to one image region so that a rotation angle and an enlargement/reduction magnification of the one image region coincide with those of a reference image region which is one of the at least two image regions and affine converting means for effecting affine conversion on the image data stored in the temporary memory means based on the result of the template matching effected by the template matching means, the template matching means being constituted so as to effect template matching on the micro region image data corrected by the data correcting means and the micro region image data in the image data corresponding to the reference image region.

16. An image processing apparatus in accordance with claim 15 wherein the image data are image data produced from the same object under different conditions.

17. An image processing apparatus in accordance with claim 15 which further comprises inter-image calculating means for effecting inter-image calculation processing on the image data which have been subjected to affine conversion and the image data corresponding to the reference image region.

18. An image processing apparatus in accordance with claim 17 wherein the image data are image data produced from the same object under different conditions.

* * * * *